US009259442B2

(12) United States Patent
Philippart

(10) Patent No.: US 9,259,442 B2
(45) Date of Patent: Feb. 16, 2016

(54) METHOD AND MEANS FOR PRODUCING TISSUES AND TISSUES OBTAINED

(76) Inventor: Pierre Philippart, Brussels (BE)

(*) Notice: Subject to any disclaimer, the term of this patent is extended or adjusted under 35 U.S.C. 154(b) by 671 days.

(21) Appl. No.: 13/148,281

(22) PCT Filed: Feb. 5, 2010

(86) PCT No.: PCT/EP2010/051442
§ 371 (c)(1),
(2), (4) Date: Oct. 13, 2011

(87) PCT Pub. No.: WO2010/089379
PCT Pub. Date: Aug. 12, 2010

(65) Prior Publication Data
US 2012/0027740 A1 Feb. 2, 2012

(30) Foreign Application Priority Data
Feb. 5, 2009 (EP) .................... 091521849

(51) Int. Cl.
A61K 35/28 (2015.01)
A61K 35/16 (2015.01)
C12N 5/00 (2006.01)
A61K 9/00 (2006.01)
A61K 38/36 (2006.01)
A61K 38/48 (2006.01)

(52) U.S. Cl.
CPC . *A61K 35/28* (2013.01); *A61K 9/00* (2013.01); *A61K 35/16* (2013.01); *A61K 38/36* (2013.01); *A61K 38/4846* (2013.01); *C12N 5/00* (2013.01); *A61K 2300/00* (2013.01)

(58) Field of Classification Search
CPC ....... A61K 35/19; A61K 35/28; A61K 35/16; A61K 38/19; A61K 38/18; A61K 38/4833; A61K 31/375; A61K 9/0019; A61K 38/4846; A61K 9/00; A61K 38/36; A61K 2300/00; A61M 2202/0427; C12N 5/0663; C12N 2502/115; C12N 5/0668; C12N 5/0607; C12N 5/0665; C12N 5/00
See application file for complete search history.

(56) References Cited

U.S. PATENT DOCUMENTS

| | | | |
|---|---|---|---|
| 5,811,094 | A | 9/1998 | Caplan et al. |
| 6,719,901 | B2 | 4/2004 | Dolecek et al. |
| 6,855,119 | B2 | 2/2005 | Rivera et al. |
| 6,930,094 | B1 | 8/2005 | Nawroth et al. |
| 2003/0125255 | A1 | 7/2003 | Sorensen et al. |
| 2003/0232753 | A1 | 12/2003 | Thorpe et al. |
| 2004/0213777 | A1 | 10/2004 | Baugh et al. |
| 2006/0079440 | A1 | 4/2006 | Kehrel |
| 2007/0141036 | A1 | 6/2007 | Gorrochategui Barrueta et al. |
| 2007/0172472 | A1 | 7/2007 | Nayak |
| 2007/0276352 | A1 | 11/2007 | Crocker et al. |
| 2008/0089867 | A1 | 4/2008 | Fernandes et al. |
| 2008/0248081 | A1 | 10/2008 | Mishra |
| 2008/0268064 | A1 | 10/2008 | Woodell-May |
| 2008/0306431 | A1 | 12/2008 | Yoo |

FOREIGN PATENT DOCUMENTS

| | | |
|---|---|---|
| EP | 1 239 894 A1 | 3/2005 |
| WO | WO 00/61256 | 4/2000 |
| WO | WO 01/25413 A1 | 4/2001 |
| WO | WO 02/080991 A2 | 10/2002 |
| WO | WO 03/106040 A2 | 12/2003 |
| WO | WO 2004/002539 A2 | 1/2004 |
| WO | WO 2004/024198 A1 | 3/2004 |
| WO | WO 2007/044874 A2 | 4/2007 |
| WO | WO 2008/064487 A1 | 6/2008 |
| WO | WO 2009/114860 A2 | 9/2009 |
| WO | WO 2009/146746 A1 | 12/2009 |

OTHER PUBLICATIONS

Carter et al. Platelet-rich plasma gel promotes differentiation and regeneration during equine wound healing. Experimental and Molecular Pathology 74 (2003) 244-255.*
Asada et al. Prevention of corticosteroid-induced osteonecrosis in rabbits by intra-bone marrow injection of autologous bone marrow cells. Rheumatology 2008;47:591-596.*
Lin et al. Controlled Release of PRP-Derived Growth Factors Promotes Osteogenic Differentiation of Human Mesenchymal Stem Cells. Proceedings of the 28th IEEE EMBS Annual International Conference New York City, USA, Aug. 30-Sep. 3, 2006. p. 4358-4361.*
Kocaoemer et al. Human AB Serum and Thrombin-Activated Platelet-Rich Plasma Are Suitable Alternatives to Fetal Calf Serum for the Expansion of Mesenchymal Stem Cells from Adipose Tissue. STEM CELLS 2007;25:1270-1278.*
Camerer et al. Cell Biology of Tissue Factor, The Principal Initiator of Blood Coagulation. Thrombosis Research, vol. 81, No. 1, pp. 1-41, 1996.*
Vogel et al. Platelet-rich plasma improves expansion of human mesenchymal stem cells and retains differentiation capacity and in vivo bone formation in calcium phosphate ceramics. Platelets, Nov. 2006; 17(7): 462-469.*
Bogdanov et al. Alternatively spliced human tissue factor: a circulating, soluble, thrombogenic protein. Nature Medicine, vol. 9. No. 4 Apr. 2003. p. 458-462.*
Daubie et al., "Tissue factor: a mini-review," *Journal of Tissue Engineering and Regenerative Medicine* (2007) 1:161-169. XP002504742.

(Continued)

*Primary Examiner* — Taeyoon Kim
(74) *Attorney, Agent, or Firm* — Merchant & Gould P.C.

(57) ABSTRACT

A method regenerates specific tissue, preferably mesenchymal tissues like bone, fat, tendon, muscle, cartilage and marrow stroma and hematological tissue (RBC, WBC, platelets, lymphocytes, hematological stem cells (HSC), endothelial progenitor cells (EPC) etc.). A method for reconstructing, regenerating, rejuvenating or reinforcing a damaged or diseased tissue in a mammal subject, and preferably a human patient, uses a (regenerated) tissue obtained by this method.

11 Claims, 12 Drawing Sheets

(56) References Cited

OTHER PUBLICATIONS

Philippart et al., "Human recombinant tissie factor, platelet-rich plasma, and tetracycline induce a high-quality human bone graft: A 5-year survey," *The International Journal of Oral & Maxillofacial Implants* (2003) 18: 411-416. XP009026409.

Graziani et al., "The in vitro effect of different PRP concentrations on osteoblasts and fibroblasts", *Clin Oral Implants Res.*, vol. 17(2), 2006, pp. 212.

Harris et al., "Comparison of bone graft matrices for human mesenchymal stem cell-directed osteogenesis", *J Biomed Mater Res*, vol. 68A, 2004, pp. 747-755.

Inane et al., "Osteogenic Induction of Human Periodontal Ligament Fibroblasts Under Two- and Three-Dimensional Culture Conditions", *Tissue Engineering*, vol. 12, No. 2, 2006, pp. 257-268.

Lucarelli et al., "Platelet-derived growth factors enhance proliferation of human stromal stem cells", *Biomaterials*, vol. 24, 2003, pp. 3095-3100.

Mariani et al., "Characterization of Tissue-Engineered Scaffolds Microfabricated with PAM", *Tissue Engineering*, vol. 12, No. 3, 2006, pp. 547-559.

Yamada et al., "Tissue-engineered injectable bone regeneration for osseointegrated dental implants", *Clin Oral Implants Res.* vol. 15(5), 2004, pp. 589-597.

\* cited by examiner

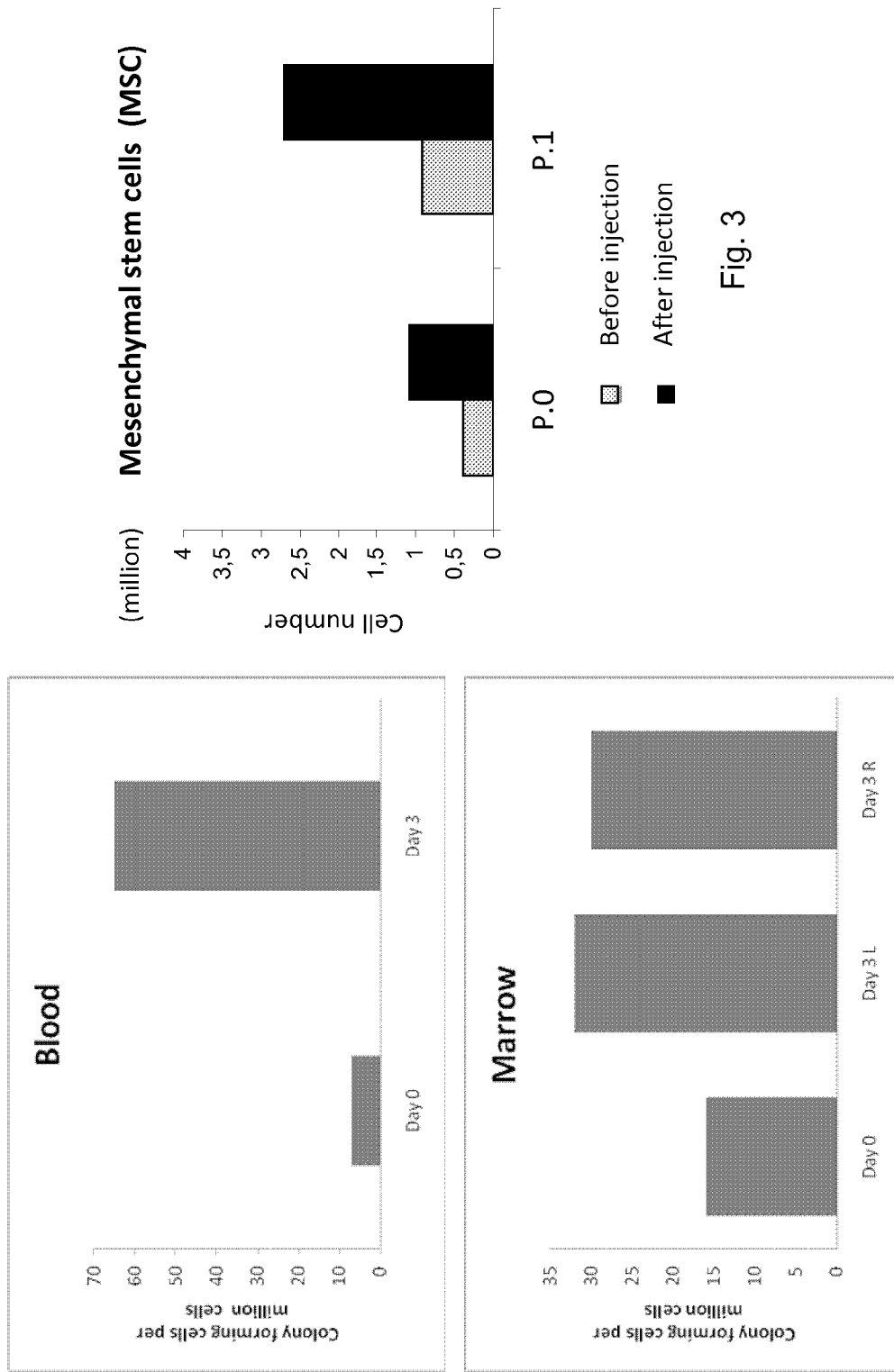

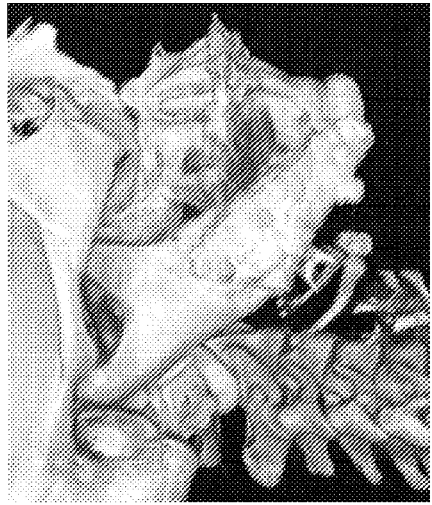
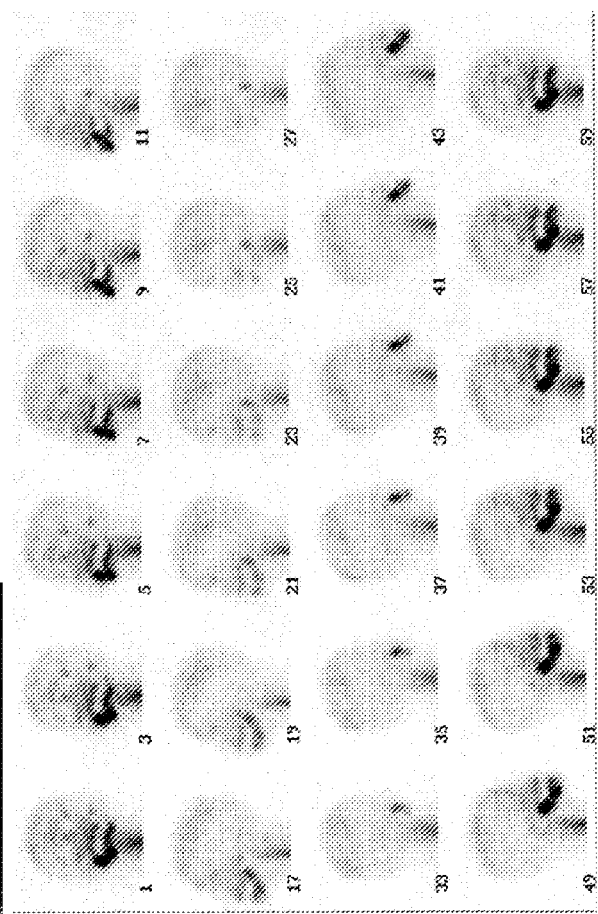
Fig. 13

METHOD AND MEANS FOR PRODUCING TISSUES AND TISSUES OBTAINED

This application is a National Stage Application of PCT/EP2010/051442, filed 5 Feb. 2010, which claims benefit of Ser. No. 09/152,184.9, filed 5 Feb. 2009 in the EPO and which applications are incorporated herein by reference. To the extent appropriate, a claim of priority is made to each of the above disclosed applications.

FIELD OF THE INVENTION

The present invention is related to the field of tissue production (regeneration, reconstruction, reinforcement and/or rejuvenation).

More precisely, the present invention is related to a method and means (products and device) for regenerating specific tissue or cells, preferably mesenchymal tissues like bone, fat, tendon, muscle, cartilage and marrow stroma and hematological tissue or cells (RBC, WBC, platelets, lymphocytes, hematological stem cells; HSC), endothelial progenitor cells; EPC) etc.).

The present invention is also related to a method and means (products and device) for reconstructing, regenerating, rejuvenating or reinforcing a damaged or diseased tissue or cells in a mammal subject, preferably a human patient, using a (regenerated) tissue or cells obtained by the method of the invention.

STATE OF THE ART

There are different techniques for reconstructing damaged or diseased tissues, and namely bones. Cell-mediated regenerative technique is one of them.

Mesenchymal stem cells (MSC), or HSC correspond to stem cells found in bone marrow stroma known as "mesenchyme" and also found in fat tissues.

MSC and HSC can be expanded in ex vivo cultures to obtain an appropriate number of cells. However, the collection of a large amount of bone marrow and a long time of culture are required in order to obtain a sufficient amount of stem cells. The in vitro culture of stem cells alters their capacity to proliferate and reduces their differentiation potential. These cells present multi-potentiality for differentiation and multiplication and can be made to differentiate into various types of cells, such as muscle, vasculature, neuronal tissue, liver, osteoblasts, chondrocytes, myoblasts, keratinoblasts and fibroblasts using adequate cytokines and growth factors and hematological cells comprising EPC.

It has logically been proposed to use these MSC in cell-mediated regenerative technique.

Furthermore, it is known that aging modifies stem cells properties and their differentiation capacity.

Practically, in bone regeneration method, MSC are extracted from a patient, made to proliferate and to differentiate in vitro into osteoblasts using appropriate bone growth factors. Thus bone tissue is generated and then is used as an implant for implantation to the patient in a reconstruction method. After a heart attack, the patient is locally anaesthetized to collect a large amount of bone marrow sample, which is re-injected in total or partially, or after cell sorting. In cancer therapy, stem cells can be isolated and stimulated and possibly transfected ex-vivo, before their re-injection to the patient. As adjuvant for transplantation for the treatment of leukemias, large amounts of heterologous MSC are injected together with the donor bone marrow.

Research for the potential use of platelet-rich plasma (abbreviated "PRP") in tissue regeneration and tissue reconstruction has already been initiated.

It has been proven that PRP is able to induce in vitro proliferation of stromal stem cells (Lucarelli E. et al. *Biomaterials* 24 (2003), pp. 3095-3100).

Recent scientific studies have also given the first results concerning the beneficial effect of platelet-rich plasma (abbreviated "PRP") used as graft material with MSC in bone reconstruction (Kitoh H. et al. *Clin. Oral Implants Res.*, vol. 15(5) (2004), pp. 589-597; Yamada Y et al. *J. Biomed. Mater. Res.*, vol. 68A(4) (2004), pp. 747-755).

Nevertheless, the current methods of tissue regeneration using MSC-HSC and the HSC cells present several drawbacks. In particular, it is difficult with these methods and cells to give generated bone tissue an appropriate shape. It is also difficult to obtain a bone tissue with sufficient mechanical strength to withstand implantation. Moreover, in vitro culture is very time consuming for obtaining a bone tissue in sufficient quantity.

SUMMARY OF THE INVENTION

The present invention provides an improved and alternative method and means for obtaining and/or inducing proliferation of (non human embryonic) stem cells (preferably MSC and EPC and possibly to the exclusion of HSC) and for "production" (regeneration, reconstruction, reinforcement and/or rejuvenation) of mammal tissues or cells which do not present the drawbacks of prior art.

Preferably, MSC are defined as expressing (at their cell surface) 1, 2 or (preferably) three positive markers selected from the group consisting of CD105, CD73, CD90 and lacking the expression (at their cell surface) of 1, 2, 3, 4 or (preferably) 5 markers selected from the group consisting of CD45, CD34, CD14, CD19 and HLA-DR.

Alternatively (or in addition), MSC are plastic-adherent cells when maintained in standard culture conditions.

Alternatively (or in addition), MSC are able to differentiate to osteoblasts, adipocytes and/or chondrocytes in vitro.

Preferably, EPC are defined as expressing (at their cell surface) both CD133 and CD34 and preferably further express CD31 and/or CD144, but possibly not CD45.

Alternatively (or in addition), EPC are defined by their ability to form colonies in vitro, wherein preferably a colony is defined as a central core of round cells with more elongated sprouting cells at the periphery.

Alternatively (or in addition), EPC are defined by their angiogenic properties when plated in matrigel assay in the presence of VEGF.

Preferably, HSC are defined as expressing CD34 and CD45 markers.

The present invention proposes a method and means which reduces or avoids possible graft versus host and host versus graft rejection and also infection drawbacks following tissue or cells regeneration, reconstruction or reinforcement of damaged or diseased tissues in a mammal subject, including a human patient.

The present invention further proposes an improved and simplified method and means, which may not require any general anesthesia, that is especially harmful in the case of elder patients or of those suffering from heart attack or injuries.

Advantageously, the products, methods and means of the present invention are used for regenerating tissues or cells.

In particular, the present invention provides a method and means which allow obtaining a new (bone) tissue with satisfying structural and physical characteristics for a (bone) reconstruction. These physical characteristics namely include shape, mechanical strength, and elasticity. The biological characteristics namely include a high rate and concentration of immature cells with high potential of proliferation, commitment and differentiation in some mature tissues like bones, skin, fat or muscles.

The present invention also provides a method and means for a treatment of heart attacks, which mobilize stem cells, by an induction in the bone marrow of a high concentration of immature stem cells comprising MSC and possibly EPC (possibly with the exclusion of HSC) and/or by an induction in the blood of a high concentration of EPC cells.

In practice, all inflammatory status like after surgery procedures or inflammatory diseases may also benefit from the present method and means, since inflammation naturally mobilizes stem cells, and since an increase in stem cells can naturally be translated into differentiated cells were there is a need.

The present invention also provides a simplified method and means that will reduce or suppress in vitro culturing time and reduce the quantity of harvested marrow needed.

The present invention is related to a method and means for obtaining stem cells (preferably MSC-EPC, possibly with the exclusion of HSC) and possibly for a regeneration, reconstruction, reinforcement and/or rejuvenation of (a) mammal subject tissue or cells, preferably (a) human patient tissue or cells, this method comprising the steps of:

a) collecting a (fluid) blood sample from this mammal subject, preferably the human patient;
b) preparing an autologous PRP from this blood (fluid) plasma sample, wherein the concentration of platelet rate of PRP is preferably comprised between about 100% and about 1000%, more preferably comprised between about 200% and about 500% of the whole blood of this mammal subject, preferably this human patient;
c) activating this autologous PRP with an effective amount of a(n active) mammal, preferably human compound selected from the group consisting of:
   thrombin (heterologous, autologous or recombinant human or bovine thrombin) including recombinant thrombin (FII) (being activated or not).
   a compound (coagulation factor) being able to produce thrombin, especially thromboplastin (tissue factor), preferably a recombinant thromboplastin (rTF), more preferably a human tissue factor (hTF), even more preferably a recombinant human tissue factor (rhTF), more specifically a recombinant soluble human tissue factor (rshTF), possibly combined with the addition of phospholipids (PL), such as phosphatidylcholine, phosphatidylserine and phosphatidylethanolamine,
   $CaCl_2$,
   a (recombinant) human Factor VII or Factor VIIa (such as the compound NOVOSEVEN®),
   a (recombinant) human Factor X(a),
   a (recombinant) tissue Factor and (recombinant) Factor VII or (recombinant) Factor VIIa,
   (recombinant) tissue factor and Factor Xa,
   (recombinant) tissue Factor/Factor-VIIa/Factor Xa,
   (recombinant) Factor VIII;
   (recombinant) Factor IX, or
   a combination of the above mentioned compounds; so as to obtain a first fluid (solution) containing concentrated activated autologous platelet-rich plasma;
d) selecting in the same mammal subject, preferably the same human patient, a target injection area rich in non embryonic (preferably MSC, EPC) stem cells (preferably a bone marrow from sternum or iliac crest) or a fat tissue;
e) injecting this first fluid (solution) into this target injection area of the mammal subject, preferably the human patient, so as to locally induce in this mammal subject, preferably in this human patient, an in vivo proliferation of (preferably MSC-EPC) stem cells;
f) (possibly) after a sufficient incubation time, from the same mammal subject, preferably the same human patient, collecting either a bone marrow (fluid) sample rich in (MSC, EPC) cells from this target injection area, or a blood (fluid) sample from this mammal, or a fat sample from this mammal, and recovering from this sample stem cells;
   possibly repeating step a) to step e) or step a) to step
   f) several times, preferably at least two times, three times or four times, at defined time intervals (preferably every week);
g) possibly collecting a second blood (fluid) sample;
h) possibly preparing a second autologous platelet rich plasma from this second blood (fluid) sample;
i) possibly activating this autologous platelet rich plasma by addition of an effective amount of the above mentioned active compound added in step c) so as to obtain a second fluid (solution) containing concentrated activated autologous platelet rich plasma from this second blood (fluid) sample;
j) possibly mixing this second fluid (solution) and the bone marrow or blood (fluid) or fat sample rich in stem cells and previously collected, so as to obtain a composition comprising activated concentrated autologous platelet rich plasma and stem cells;
k) possibly adding differentiation adjuvants to these stem cells, preferably to the composition (comprising activated concentrated autologous PRP and stem cells), wherein these adjuvants comprise the above mentioned active compound(s) used in step c) and/or at least one matrix for cell anchoring and one or more elements for obtaining (inducing) differentiation of stem cells into specific cells, such as osteoblastic cells (osteocytes, osteoblasts, . . . ), muscle cells, endothelial cells, neuronal cells, hepatocytes, or fibroblasts and keratinocytes, wherein these elements being preferably selected from the group consisting of vitamins (vitamin C (L-Ascorbic acid), vitamin D3 (1,25 (OH)2D3 vitamin), cortisone (or cortisone derivatives, such as dexamethasone, hydrocortisone, prednisolone, methylprednisolone, dexamethasone, triamcinolone betamethasone) and possibly β-glycerophosphate (these elements are preferably present in poly DL-lactic-co-glycolic acid (PLGA), polyglycolic acid and/or poly-L-lactic acid (PLLA), alginate scaffolds (such as microbeads) allowing a slow release of the elements), and/or $BMP_2$ (possibly obtained from MEDTRONICS), or epidermal-growth factor, or neural-growth factor or any other cytokine, growth- or differentiation-factor known by the person skilled in the art so as to induce a differentiation of the (MSC, EPC with the possible exclusion of HSC) stem cells into "predefined" differentiated tissue cells and possibly obtaining a regeneration of the desired tissue and,
l) possibly adding to the composition comprising activated concentrated autologous platelet rich plasma and stem cells, an adequate gelling agent (this gelling agent being preferably obtained from a sufficient amount of the active compound added in step c) to obtain a gel and,
m) possibly using the obtained gel as implant by possibly applying the gel thus obtained into/onto a target reconstruction site (such as an autologous harvested bone, an allograft, a xenograft or a collagen leaf) of the mammal subject, preferably the human patient, so that a tissue reconstruction can take place at this reconstruction site.

The steps a) to m) can be repeated several times (preferably at least two, three or four times) at defined time intervals (preferably every week), so as to obtain sufficient amount of stem cells.

The invention further relates to a method for obtaining a (mononuclear) cell (MSC) population enriched in activated MSC comprising the steps of:
optionally activating bone marrow stem cells, preferably by the method of the invention and/or by the addition of the PRP and the coagulation factor;
obtaining a sample of activated bone marrow;
optionally enriching stem cells of this sample.

Preferably in this method for obtaining a (mononuclear) cell (MSC) population enriched in activated MSC, the capacity of these MSC to form colonies (when grown in vitro) (CFU-F) is increased, more preferably by at least about 30% (at least about 50%, still more preferably by at least about 100%).

Advantageously, or in addition, in this method for obtaining a (mononuclear) cell (MSC) population enriched in activated MSC, at least about 13 (more preferably at least about 15, still more preferably at least about 20) colonies (CFU-F) are formed upon the in vitro culture of 1 000 000 mononuclear cells obtained from a sample from this activated bone marrow.

Advantageously, or in addition, in this method for obtaining a (mononuclear) cell (MSC) population enriched in activated MSC, at least about 35% (more preferably at least about 40%, still more preferably at least about 50%) of the colonies formed upon the (in vitro) culture of MSC (CFU-F) express osteogenic markers, such as alkaline phosphatase.

Preferably in this method for obtaining a (mononuclear) cell (MSC) population enriched in activated MSC, the enrichment of stem cells is performed by centrifugation of the bone marrow sample (yielding a fluid supernatant, a pellet enriched in non MSC cells and debris and an intermediate fraction enriched in (activated) MSC cells) and by a recovering of this intermediate fraction.

Another aspect of the present invention relates to a bone marrow sample comprising a (an increased) population of activated MSC, wherein preferably the capacity of this (activated) MSC to form colonies (when grown in vitro) (CFU-F) is increased, more preferably by at least about 30% (more preferably by at least about 50%, still more preferably by at least about 100%).

Advantageously (or in addition), in this bone marrow sample comprising a (an increased) population of activated MSC, at least about 13 (at least about 15, still more preferably at least about 20) colonies (CFU-F) are formed upon an in vitro culture of 1 000 000 mononuclear cells obtained from this sample (preferably obtained from this activated bone marrow).

Advantageously (or in addition), in this bone marrow sample enriched in an activated MSC population, at least 35% (more preferably at least about 40%, still more preferably at least about 50%) of the colonies formed by the culture of MSC (CFU-F) express osteogenic markers, such as alkaline phosphatase.

Possibly, in this method for obtaining a MSC population enriched in activated MSC and/or in this bone marrow sample enriched in activated MSC, the (relative) content of EPC is not increased and/or the content of HSC is decreased.

The MSC cells obtained by the method of the invention are advantageously injected to a mammal subject, preferably a human patient, preferably close (or at) the site to regenerate or, alternatively, by blood infusion.

The method according to the invention could be used for regenerating tissue of damaged or diseased tissue or for recovering specific stem cells used as screening cells for characterizing the effect of toxic compounds, or to store (in banks) for future use, be it autologous or heterologous.

According to the invention, the terms "tissue regeneration" refer to the regeneration of a new tissue from a stem cell and the term "reconstruction" or "reinforcement" is defined as the implantation and integration of this obtained regenerated tissue into a mammal subject, preferably a human patient, where tissue repair or tissue growth stimulation is needed. The tissue repair or stimulation may be required because of damages, diseases or weakness (ageing state) affecting the patient's tissues or affecting the general systemic health state of the patient. Tissue regeneration is particularly needed in the case of cancer, cardiomyopathy, congenital heart disease, coronary artery disease, ischemia, diastolic dysfunction, endocarditis, myocardial infarction, Parkinson disease, Alzheimer disease, Huntington disease, Tay-Sachs disease, spinal cord injury, stroke, cerebrovascular accident, aplastic anemia, multiple sclerosis, rheumatoid arthritis, Sjorgen syndrome, diabetes mellitus 1, Graves' disease, lupus erythematosus, bone reconstruction, bone atrophy, osteoporosis and bone reinforcement and possibly atherosclerosis and myocarditis.

Therefore, the terms "reconstruction site" refer to a specific site of a tissue, inside a mammal where tissue reconstruction for repairing or reinforcement purpose is required.

According to the invention, a "platelet-rich plasma (PRP)" means a fluid (solution) wherein the concentration of platelets has been increased by a percentage of at least about 100%, preferably between about 200% and 1000% over the baseline venous count of the treated mammal subject (human patient), and reach a platelet concentration of at least 600.000 (per microliter: µL), at least 800.000 per µl or at least 1.000.000 platelets per µL, preferably between about 800.000 per µL (or about 1.500.000 platelets) and about 6.000.000 per µL (or about 8.000.000 platelets), more preferably between about 2.000.000 platelets per µL and about 5.000.000 platelets per µL. PRP is advantageously obtained with a centrifugation device, such as the one described in the documents U.S. Pat. No. 6,719,901, WO02/080991, U.S. Pat. No. 6,855,119, WO03/106040, WO00/61256 and WO2004/024198.

Graziani F. et al., *Clinical oral implant research*, Vol. 17, Issue no. 2, pp. 212-219 (2006) have tested the effects of different PRP concentrations on cell proliferation. It seems that the maximum effect was achieved at a concentration of 2.5 fold with a higher concentration resulting in a reduction of cell proliferation. The most notable effect of PRP on cell proliferation was characterized at about 72 hours. This platelet concentration was approximately half of the maximum concentration that could be obtained. However, for some cell proliferations, higher concentrations of PRP could be preferred.

The thrombin can be advantageously autologous, heterologous or recombinant thrombin, preferably a recombinant thrombin, such as the one produced by the Company ZYMOGENETICS (www.zgi.com).

Preferably, from about 10 to about 200 units of (recombinant, bovine or autologous) thrombin, more preferably, about 10 to about 75 units of (recombinant) thrombin are added to 6 to 20 ml of anticoagulated (inactivated) PRP.

Therefore, to induce a very slow coagulation of PRP, (recombinant, bovine or autologous) thrombin is added to anticoagulated (inactivated) PRP from about 0.5 unit/ml to about 33 units/ml, preferably from about 0.5 unit/ml to about 3.75 units/ml, more preferably from about 1.5 units/ml to about 3.75 units/ml.

Alternatively, to induce a slow coagulation of PRP (recombinant, bovine or autologous) thrombin is added to anticoagulated (inactivated) PRP from about 0.5 unit/ml to about 10 units/ml, preferably from about 1.5 units/ml to about 10 units/ml.

A thrombin unit is the substance that clots 1 ml of oxalated plasma in 30 sec at 37° C.

Other coagulation factors involved in mammal clotting (Factor VII, Factor VIIa (NovoSeven® from Novonordisk), Factor VIII, Factor IX, Factor X, Factor Xa, etc.) or any compound involved in clotting (or able to generate thrombin) can be also used. However, the thromboplastin (human tissue factor: hTF or hTf) is preferred, because it is safe, can be presented in a soluble form and contrary to thrombin, coagulation cascade can be controlled and a coagulation clotting is less rapidly obtained. Examples of associated lipids and other molecules possibly present in the composition are described in EP 1239894.

Preferably, the PRP and the coagulation factor (more preferably being soluble human Tissue factor; shTf) are mixed (shortly) before injection to a patient.

Advantageously, the PRP and the coagulation factor (more preferably being soluble human Tissue factor: shTf) are mixed (preferably at temperatures comprised between about 20° C. and about 37° C.) and remain soluble, preferably for several minutes (at temperatures comprised between about 20° C. and about 37° C.)

More preferably, the PRP when mixed with the coagulation factor (more preferably being shTf) coagulates very slowly, preferably remains (or is able to remain) liquid (soluble) when mixed for more than 1 minute, more preferably for more than 2, 3, 4 or even 5 minutes (the temperature being comprised between about 20° C. and about 37° C.)

Even more preferably, the PRP when mixed with the coagulation factor (more preferably being shTf) coagulates very slowly, preferably remains (or is able to remain) liquid (soluble) when injected to the mammal subject (human patient) for more than 30 seconds, more preferably for more than 1, 2, 3, 4 or even 5 minute(s).

Preferably from about 600 to about 120000 Units of (activated) Factor VIIa (about 12 µg to about 2400 µg), more preferably, about 600 to about 60000 units of (activated) Factor VIIa (about 12 µg to about 1200 µg), still more preferably from about 600 to about 6000 units of (activated) Factor VIIa (about 12 µg to about 120 µg) is added to 6 to 20 ml of anticoagulated (inactivated) PRP.

Therefore, (to induce a slow coagulation of PRP) (activated) Factor VIIa is added to anticoagulated (inactivated) PRP from about 30 units/ml (0.6 µg/ml) to about 20000 unit/ml (400 µg/ml), preferably from about 30 units/ml (0.6 µg/ml) to about 10000 units/ml (200 µg/ml), more preferably from about 30 unit/ml (0.6 µg/ml) to about 1000 units/ml (20 µg/ml).

Alternatively, (to induce a very slow coagulation of PRP) (activated) Factor VIIa is added to anticoagulated (inactivated) PRP from about 30 unit/ml (0.6 µg/ml) to about 6000 units/ml (120 µg/ml), preferably from about 30 units/ml (0.6 µg/ml) to about 3000 units/ml (60 µg/ml), more preferably from about 30 units/ml (0.6 µg/ml) to about 300 units/ml (6 µg/ml); still more preferably from about 100 unit/ml (2 µg/ml) to about 300 unit/ml (6 µg/ml).

It is meant by a human thromboplastin, the human tissue factor (hTF) with addition of (different) phospholipids (phosphatidyl-choline, phosphatidyl ethanol amine and/or phosphatidyl serine. This hTf can be made of the 263 amino acids of the (complete) hTf, a truncated hTf being the polypeptide of 243 amino acids (the extracytoplasmic tail and membrane portion of the tissue factor) or only the (truncated) (soluble) tissue factor, a polypeptide of 219 or 206 amino acids (extracytoplasmic tail only) or any variant thereof.

Preferably from 100 µg to 3000 µg, more preferably from about 300 µg to about 900 µg of soluble tissue factor is added to about 6 to about 20 ml of anticoagulated (inactivated) PRP.

Therefore, (to induce a very slow coagulation,) from about 2 µg/ml to about 150 µg/ml, preferably from about 15 µg/ml to about 150 µg/ml, still more preferably from about 15 µg/ml to about 45 µg/ml of soluble tissue factor is added to anticoagulated (inactivated) PRP.

Alternatively, (to induce a slow coagulation of PRP) from about 15 µg/ml to about 500 µg/ml, preferably from about 50 µg/ml to about 150 µg/ml, of soluble tissue factor is added to anticoagulated (inactivated) PRP.

The variant of the (not modified) hTf can comprise a deletion, addition or substitution of one or more amino acids which do not affect the functional activity (activation of PRP) of the not modified molecule.

Activation of PRP can also be obtained by other molecules involved in coagulation cascade, preferably one of the active compound used in step c) of the above mentioned method.

These various active compounds, especially the coagulation factors could be submitted to one or more inactivation steps in order to avoid the transmission of one or more contaminants, especially bacteria or viruses. This inactivation step could be based upon addition of solvent/detergent, dry heat, UVC inactivation, etc.

In the method of the invention especially in the step k) of the above described method, micro beads are used as drug deliveries system in which the surface layer contains cortisone, in which the medium layer contains ascorbic acid and in which the internal layer coating comprises betaglycerophosphate.

Other modifications of these micro beads could be used in the method according to the invention for improving the differentiation of stem cells, in particular for their recruitment to a selected site and their commitment, differentiation into desired cells, such as muscle cells, vessel cells, neuronal cells, hepatocytes, osteoclasts, fibroblasts, etc.

In a preferred embodiment, in the method according to the invention, the steps a), b) and c) are not performed and the steps d) and e) are modified as follows:
 d) selecting in a mammal subject, preferably in the bone marrow of a human patient, a target injection area rich in stem cells (preferably the sternum or the iliac crest of the mammal),
 e) injecting in this target injection area of the mammal subject (human patient), a sufficient amount of a stem cell activation fluid or the active compound, used in step c) so as to locally induce in the mammal subject (preferably in the human patient), directly an in vivo proliferation of (mesenchymal) stem cells without the addition of autologous PRP.

The other steps f) to m) of the preferred embodiment of the method may correspond to the ones above-described.

In another preferred embodiment, the steps f) to m) are not performed and the steps a) to e) are used for obtaining proliferation of stem cells in the body of a mammal subject (human patient), especially in old persons (above 50 years, preferably about 60 years or above 65 years) which have low concentration of stem cells. This rejuvenation step by a stimulation of the stem cells is performed, preferably before a possible chirurgical operation upon the body of a (human)

patient in order to improve regeneration, reconstruction, reinforcement or rejuvenation of a tissue or cells, especially a damaged or diseased tissue or cells in this human patient body.

If necessary, said stimulation could be obtained as described in the previous embodiment without using the steps a) to c) and by selecting steps d) and e) as above suggested, without the addition of PRP.

In the method according to the invention, after a sufficient incubation time, the person skilled in the art may collect either a bone marrow (fluid) sample rich in stem cells, preferably from the target injection area or for a blood (fluid) sample which is also rich in (EPC, MSC) stem cells.

This recovering step (f) could be done upon the blood (fluid) sample due to the fact that the in vivo proliferation of stem cells has also induced the propagation of these stem cells into the blood of the mammal subject. Therefore, it is possible to recover stem cells directly from a blood (fluid) sample, by methods well known by the person skilled in the art, such as classical plasmapheresis dialysis method and means.

The present invention provides (non coagulated and/or soluble) PRP and a (sufficient amount of a) coagulation factor or a (pharmaceutical) composition comprising them as a medicament, preferably in the form of a non coagulated and/or soluble mixture of PRP and a coagulation factor.

Preferably, the PRP and the coagulation factor (more preferably being shTf) are mixed (shortly) before injection to a patient.

More preferably, the PRP when mixed with the coagulation factor (more preferably being shTf) coagulates very slowly, preferably remains (or is able to remain) liquid (non coagulated and/or soluble) for more than 1 minute, more preferably for more than 2, 3, 4 or even 5 minutes.

By a sufficient amount of a coagulation factor, it is meant an amount allowing a (very) slow coagulation of (inactivated) PRP.

More preferably, the present invention provides (a non coagulated and/or soluble mixture of) PRP and a coagulation factor (compound involved in clotting) selected from the group consisting of the (preferably soluble) thromboplastin (or tissue factor (TF)), the Factor Xa, the Factor VIIa or a mixture thereof or a (pharmaceutical) composition comprising them, as a medicament.

Still more preferably, the present invention provides (a non coagulated and/or soluble mixture of) PRP and this coagulation factor (compound involved in clotting) or a (pharmaceutical) composition comprising them, for use as a medicament to enrich stem cell pool of a mammal subject, preferably a human patient, preferably EPC and/or MSC and more preferably not modifying HSC pool, nor modifying hemostasis.

Alternatively, the present invention provides a coagulation factor, preferably selected from the group consisting of the (preferably soluble) thromboplastin (or tissue factor (Tf)), the Factor Xa, the Factor VIIa or a mixture thereof (more preferably soluble tissue factor (sTF), still more preferably soluble human Tissue factor (shTf)) for use as a medicament to enrich stem cell pool of a mammal subject, preferably a human patient, preferably EPC and/or MSC and more preferably not modifying HSC pool, nor modifying hemostasis.

The present invention provides for (a non coagulated and/or soluble mixture of) PRP and a coagulation factor, preferably selected from the group consisting of (soluble) thromboplastin (hTf), factor Xa and Factor VIIa, more preferably soluble hTf, or a (pharmaceutical) composition comprising them, for use as a medicament, especially the use of them for the preparation of a medicament for a treatment and/or a prevention of a cardiovascular (heart-related or cardiac) disease preferably selected from the group consisting of (degenerative) cardiomyopathy, (congenital heart disease), coronary artery disease, ischemia, diastolic dysfunction, atherosclerosis, myocarditis, endocarditis and myocardial infarction.

Alternatively, the present invention provides a coagulation factor, preferably selected from the group consisting of the (preferably soluble) thromboplastin (or tissue factor (Tf)), the Factor Xa, the Factor VIIa or a mixture thereof (more preferably soluble tissue factor (sTf), still more preferably soluble human Tissue factor (shTf)) for use as a medicament for a treatment and/or a prevention of a cardiovascular (heart-related or cardiac) disease preferably selected from the group consisting of (degenerative) cardiomyopathy, (congenital heart disease), coronary artery disease, ischemia, diastolic dysfunction, atherosclerosis, myocarditis, endocarditis and myocardial infarction.

The present invention provides for (a non coagulated and/or soluble mixture of) PRP and a coagulation factor, preferably selected from the group consisting of (soluble) thromboplastin (hTf), factor Xa and Factor VIIa, more preferably soluble hTf, or a (pharmaceutical) composition comprising them, for use as a medicament for a treatment and/or a prevention of a neurological disease, preferably selected from the group consisting of Parkinson disease, Alzheimer disease, Huntington disease, Tay-Sachs disease, spinal cord injury, stroke and cerebrovascular accident and amyotrophic lateral sclerosis (ALS).

Alternatively, the present invention provides a coagulation factor, preferably selected from the group consisting of the (preferably soluble) thromboplastin (or tissue factor (Tf)), the Factor Xa, the Factor VIIa or a mixture thereof (more preferably soluble tissue factor (sTf), still more preferably soluble human Tissue factor (shTf)) for use as a medicament for a treatment and/or a prevention of a neurological disease (of a mammal subject), preferably selected from the group consisting of Parkinson disease, Alzheimer disease, Huntington disease, Tay-Sachs disease, spinal cord injury, stroke and cerebrovascular accident and amyotrophic lateral sclerosis (ALS).

The present invention provides for (a non coagulated and/or soluble mixture of) PRP and a coagulation factor, preferably selected from the group consisting of (soluble thromboplastin (hTf), factor Xa and Factor VIIa, more preferably soluble hTf, for use as a medicament for a treatment and/or a prevention of a degenerative (auto-immune) disease, preferably selected from the group consisting of aplastic anemia, multiple sclerosis, rheumatoid arthritis, Sjorgen syndrome, diabetes mellitus 1, Graves'disease and lupus erythematosus.

Alternatively, the present invention provides for the (preferably soluble) thromboplastin (or tissue factor (Tf)), the Factor Xa, the Factor VIIa or a mixture thereof (more preferably soluble tissue factor (sTf), still more preferably soluble human Tissue factor (shTf)) for use as a medicament for a treatment and/or a prevention of a degenerative (auto-immune) disease, preferably selected from the group consisting of aplastic anemia, multiple sclerosis, rheumatoid arthritis, Sjorgen syndrome, diabetes mellitus 1, Graves'disease and lupus erythematosus.

The present invention provides for (a non coagulated and/or soluble mixture of) PRP and a coagulation factor, preferably selected from the group consisting of (soluble) thromboplastin (hTf), factor Xa and Factor VIIa, more preferably soluble hTf, or a (pharmaceutical) composition comprising them, for use as a medicament for the treatment of cancer (leukemia) and/or infectious diseases (AIDS).

Alternatively, the present invention provides for the (preferably soluble) thromboplastin (or tissue factor (Tf)), the Factor Xa, the Factor VIIa or a mixture thereof (more preferably soluble tissue factor (sTf), still more preferably soluble human Tissue factor (shTf)) for use as a medicament for the treatment of cancer (leukemia).

The present invention provides for (a non coagulated and/or soluble mixture of) PRP and a coagulation factor, preferably selected from the group consisting of (soluble) thromboplastin (hTf), factor Xa and Factor VIIa, more preferably soluble hTf, or a (pharmaceutical) composition comprising them, for use as a medicament for a treatment and/or a prevention of a bone degenerative related disease, preferably selected from the group consisting of bone atrophy, osteoporosis and possibly for bone reconstruction or bone reinforcement.

Advantageously, PRP and the coagulation factor of the invention are injected simultaneously (in the form of a non coagulated and/or soluble mixture) (or separately) into the iliac crest, the sternum and/or in adipose tissue of a mammal subject, preferably a human patient, more preferably in the bone marrow of the iliac crest of the said human patient.

Advantageously, from about 2 µg/ml to about 500 µg/ml of (soluble) hTf in about 6 to about 20 ml of PRP (in the form of a non coagulated and/or soluble mixture) is used in the medicament of the invention, preferably injected into the iliac crest, the sternum and/or adipose tissue of the subject or the patient.

Alternatively, from about 5 unit to about 500 Unit of factor Xa in about 6 to about 20 ml of PRP (in the form of a non coagulated and/or soluble mixture) is used in the medicament of the invention, preferably injected into the iliac crest or the sternum and/or adipose tissue of the subject or the patient.

Alternatively, from about 30 Unit/ml to about 20000 Unit/ml of factor VIIa in about 6 to about 20 ml of PRP (in the form of a non coagulated and/or soluble mixture) is used in the medicament of the invention, preferably injected into the iliac crest or the sternum and/or adipose tissue of the subject or the patient.

Another aspect of the present invention is a (non coagulated and/or soluble) pharmaceutical composition comprising possibly an adequate pharmaceutical carrier or diluent, an effective amount of PRP and an effective amount of a coagulation factor selected from the group consisting of:

thromboplastin (tissue factor), preferably a recombinant thromboplastin (rTf), preferably a human tissue factor (hTf), more preferably a recombinant human tissue factor (rhTf), more preferably a recombinant soluble human tissue factor (rshTf), more preferably with addition of phospholipids (PL) more specifically phosphatidylcholine, phosphatidylserine and phosphatidylethanolamine, or, Factor VII(a),
Factor X(a),
tissue Factor—Factor-VII(a),
tissue Factor—Factor VII(a)-Factor X(a),
Factor VIII(a), Factor IX(a) or a combination of the above mentioned compounds, these factors being activated or not activated, for a treatment and/or a prevention of a disease selected from the group consisting of cardiovascular diseases, neurological diseases, auto-immune diseases, inflammation, hepatic injury and/or osteoporosis.

Preferably, the (non coagulated and/or soluble) pharmaceutical composition according to the invention is used in cardiology, where cardiovascular (cardiac or heart related) disease is preferably selected from the group consisting of atherosclerosis, cardiomyopathy, congenital heart disease, myocarditis, coronary artery disease, cerebrovascular accident, diastolic dysfunction, endocarditis, ischemia and myocardial infarction.

Preferably, the (non coagulated and/or soluble) pharmaceutical composition of according to the invention is used in neurology, where the neurological disease is preferably selected from the group consisting of Parkinson, Alzheimer, Huntington, Tay-Sachs diseases, spinal cord injury, stroke, cerebrovascular accident, aplastic anemia, Amyotrophic lateral sclerosis (ALS) and/or multiple sclerosis.

Another aspect of the invention is the use of (a mixture of non coagulated (soluble)) PRP and of a coagulation factor, preferably hTf, for in vitro propagation of stem cells.

A last aspect of the present invention is related to a kit of parts comprising the various elements and means for performing the different embodiments of the method according to the invention, especially:

a centrifugation device for collecting autologous PRP and possibly means for obtaining from the plasma of a mammal, autologous thrombin or heterologous thrombin, one or more mammal, preferably human active compound(s) (coagulation factor) or fluid(s) (solutions) comprising the(se) compound(s) used in step c) of the above described method, possibly present in one or more vials, possibly means for collecting a blood sample and/or a bone marrow sample and/or a fat sample from a mammal subject and, possibly means (syringe(s), needle(s), tubing, etc) for re-injecting to the mammal subject, this autologous PRP and/or this active compound(s) at a target injection area rich in MSC.

Preferably, these means are adequate for the injection of (autologous) PRP with the MSC activation compounds (coagulation factor) or fluids comprising them and are also adequate for collecting from this target injection area rich in stem cells, a bone marrow fluid sample comprising these stem cells.

Advantageously, these means are also adequate for obtaining a connection to the centrifugation device, for collecting the obtained autologous PRP (and possibly autologous thrombin) and (simultaneously) for injecting the collected platelet rich plasma fluid (and possibly autologous thrombin) to the same patient in the target site (sternum, iliac crest or fat (adipose) tissue) rich in (mesenchymal) stem cells. These means are also used for collecting from this target injection area, a bone marrow fluid sample from the same mammal, this bone marrow fluid sample being rich in stem cells after in vivo proliferation and possibly for separating these stem cells from their contaminants, preferably by centrifugation (possibly by the centrifugation device of the kit of parts) or by means described in US 2007/0276352.

These means may also comprise suitable elements for collecting blood (fluid) samples which are rich in (mesenchymal) stem cells and for separating these stem cells from the blood (fluid) sample by means well known by the person skilled in the art, and possibly for separating these stem cells from their contaminants, preferably by a centrifugation (possibly with the centrifugation device of the kit of parts).

Preferably, these means comprise injection syringes and collecting syringes, or a dedicated device for an injection and/or collection of fluids to and/or from of bone marrow or blood, preferably the device according to the invention above described, advantageously linked to the centrifugation device, preferably a centrifugation device as described in the document WO03/106040, U.S. Pat. No. 6,855,119, WO02/080 991 and U.S. Pat. No. 6,719,901.

In the kit of parts according to the invention, the stem cells activation compounds are advantageously present in vials or syringes, or a dedicated device for injection and/or collection of fluids to and/or from bone marrow, preferably the device according to the invention above described, separated from the injection syringe comprising PRP, in order to avoid rapid coagulation. It is also possible to use a double injection syringe which allows simultaneous injection of PRP and the activation compound (coagulation factor) in the target injection area rich in stem cells (i.e. the Smarjet™ liquid and spray delivery systems sold by the Company Harvest® USA, other systems used for generation of a PRP and thrombin SMART-PREP™ of Harvest® USA, the autologous platelet separator Magellan™ of Medtronic®, the Symphony® platelet concentrated system of Depuy, the Acromed® device of Johnson and Johnson®, the Angel® of SORIN-DIDECO, the 3i platelet concentrate device or others devices used in blood banks).

The kit of parts may also comprise different vials with the different active compounds or fluids for injections, including buffers and differentiation compounds, or fluids comprising these compounds, etc.

The injection syringes or device according to the invention is adequate for injection in the sternum or in the iliac crest of a mammal subject, preferably of a human subject.

The kit of parts may also comprise other elements such as tubing, pumps, valves for allowing suitable injections, for adequate collecting from the mammal body and for allowing automatisation of the process according to the invention. These elements are advantageously integrated in an auto-transfusion system for collecting and re-injecting from a surgical site, biological compounds to the patient by suitable auto-transfusion procedures well known by the person skilled in the art.

This kit of parts may also comprise instruction means for performing the successive steps according to the invention which could be performed and/or controlled by a suitable computer and adequate software.

SHORT DESCRIPTION OF THE FIGURES

FIG. 1 represents the number of endothelial progenitor cells for $10^6$ non-adherent cells present in the patient's blood or patient's bone marrow before or after injection by the method of the invention.

FIG. 2: EPC before and after treatment.

FIG. 3 represents the number of MSC before or after injection by the method of the invention, with or without ex-vivo culture.

FIG. 4 represents the number EPC capable of forming colonies obtained from the blood or of the bone marrow of a patient before PRP+soluble hTf injection (day 0), after 3 days and after 7 days. This emphasizes the mobilization of EPC in the blood by the treatment.

Figure 7:
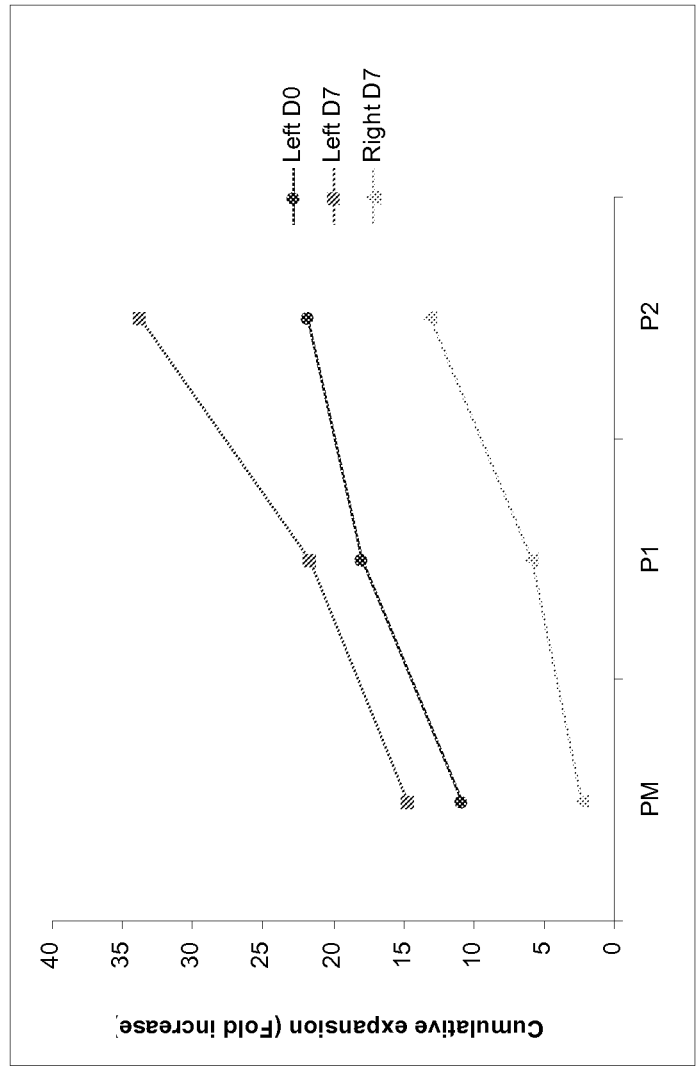

FIG. 7 represents the in vitro multiplication of MSC obtained before PRP+soluble hTf injection (day 0) or obtained after 7 days at the site of injection (left) or the opposite site (right). The expansion properties of MSC are increased by the treatment (compare left day 7 and day 0), but reduced at the opposite site.

Figure 8:
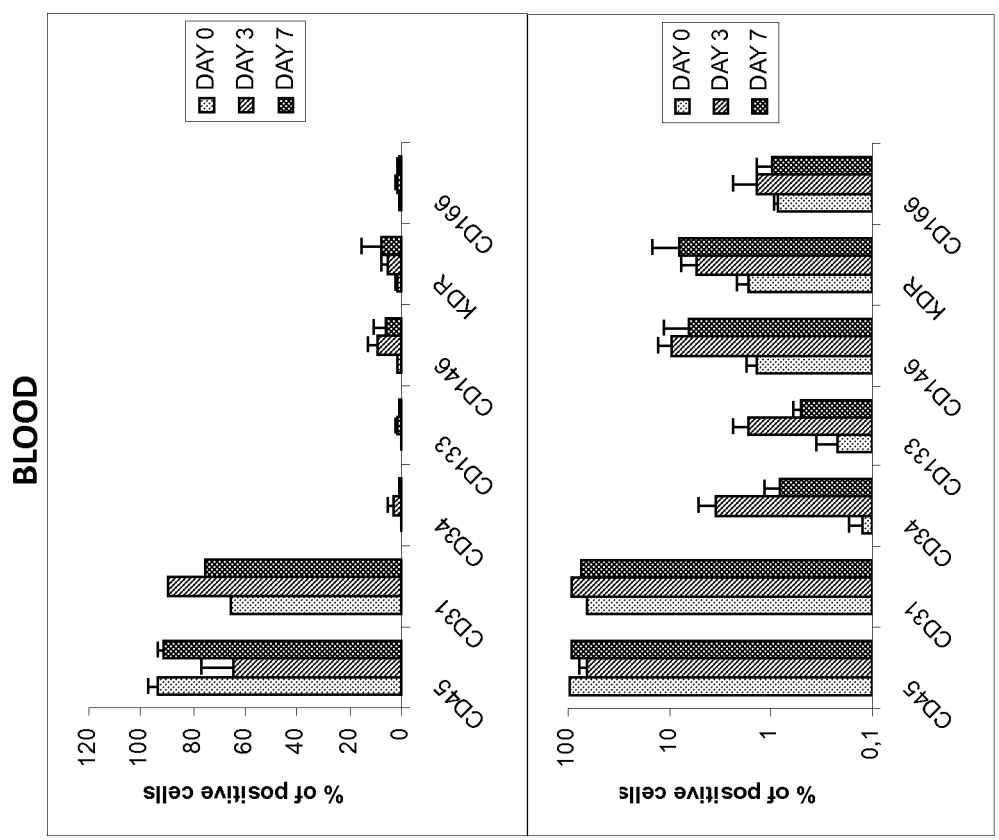

FIG. 8 represents the blood-cell population before PRP+soluble hTf treatment, after 3 and 7 days. Cells positive for CD 34 and CD 133 (stem cells) are much more abundant after 3 and 7 days of treatment, reflecting mobilization from the bone marrow.

Figure 9:
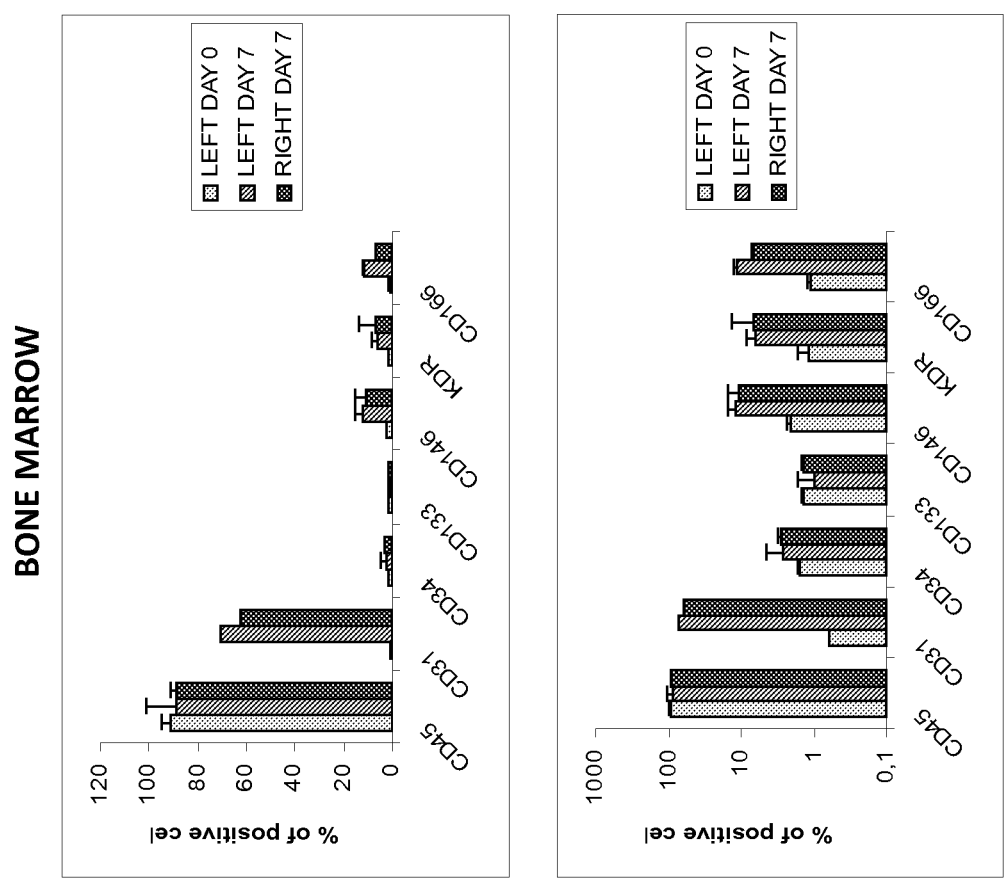

FIG. 9 represents the bone-marrow cell population obtained before PRP+soluble hTf treatment and after 7 days on the site of treatment (left) or on the opposite site. CD 34 and CD 133 levels are maintained by the treatment on both sites, emphasizing the capacity of the bone marrow to replenish stem cell content. CD 31 cells are much more abundant on both sites.

Figure 10:
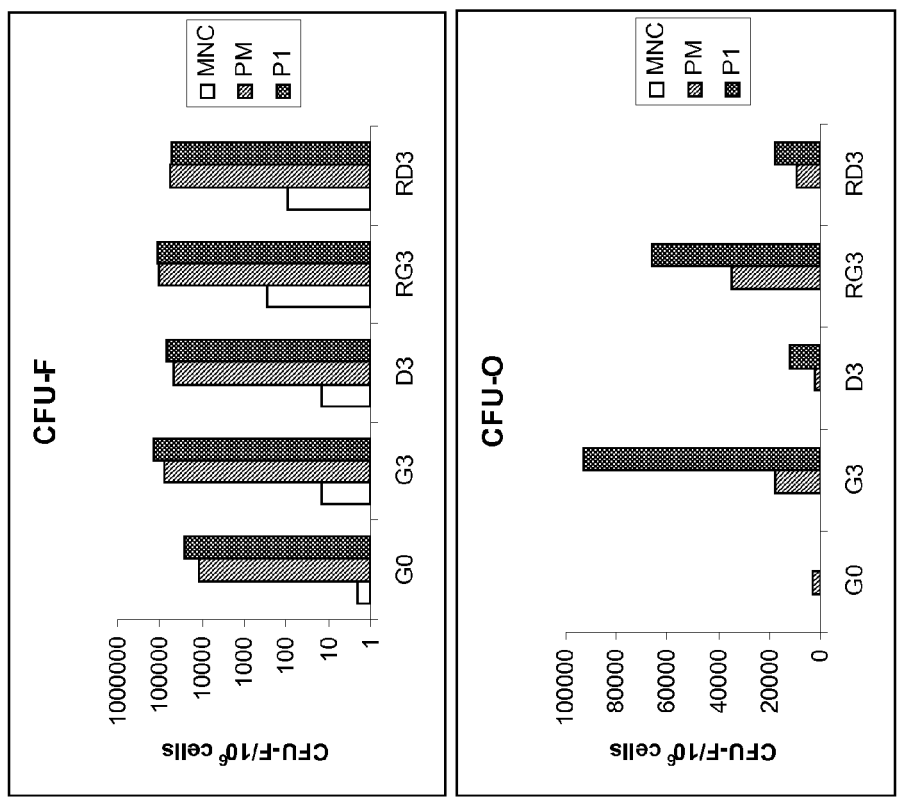

FIG. 10 represents the relative number of cells capable of forming colonies as mesenchymal precursors (CFU-F) and mesenchymal precursors expressing alkaline phosphatase considered as pre-osteoblasts (CFU-O) marker. The cells were taken from the bone marrow before (G0) treatment, after three days of PRP+soluble hTf treatment at the site of treatment (G3 and RG3) or at the opposite site (D3 and RD3). Part of cells was also treated to enrich mesenchymal cells (RG3 and RD3).

Figure 11:
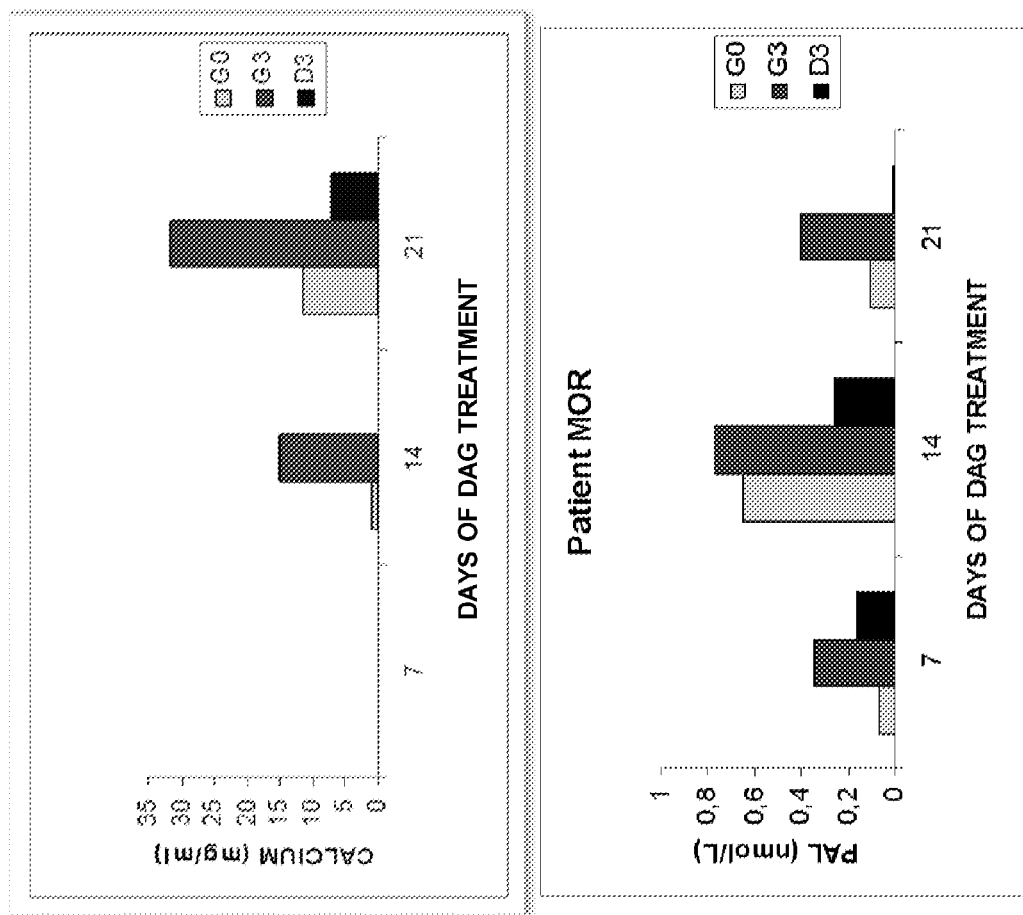

FIG. 11 represents the differentiation towards bone tissue with Calcium and alkaline phosphatase measurements. The cells were taken from the bone marrow before (G0) treatment, after three days of PRP+soluble hTf treatment at the site of treatment (G3) or at the opposite site (D3) and grown on Petri dishes for the indicated time.

Figure 12:
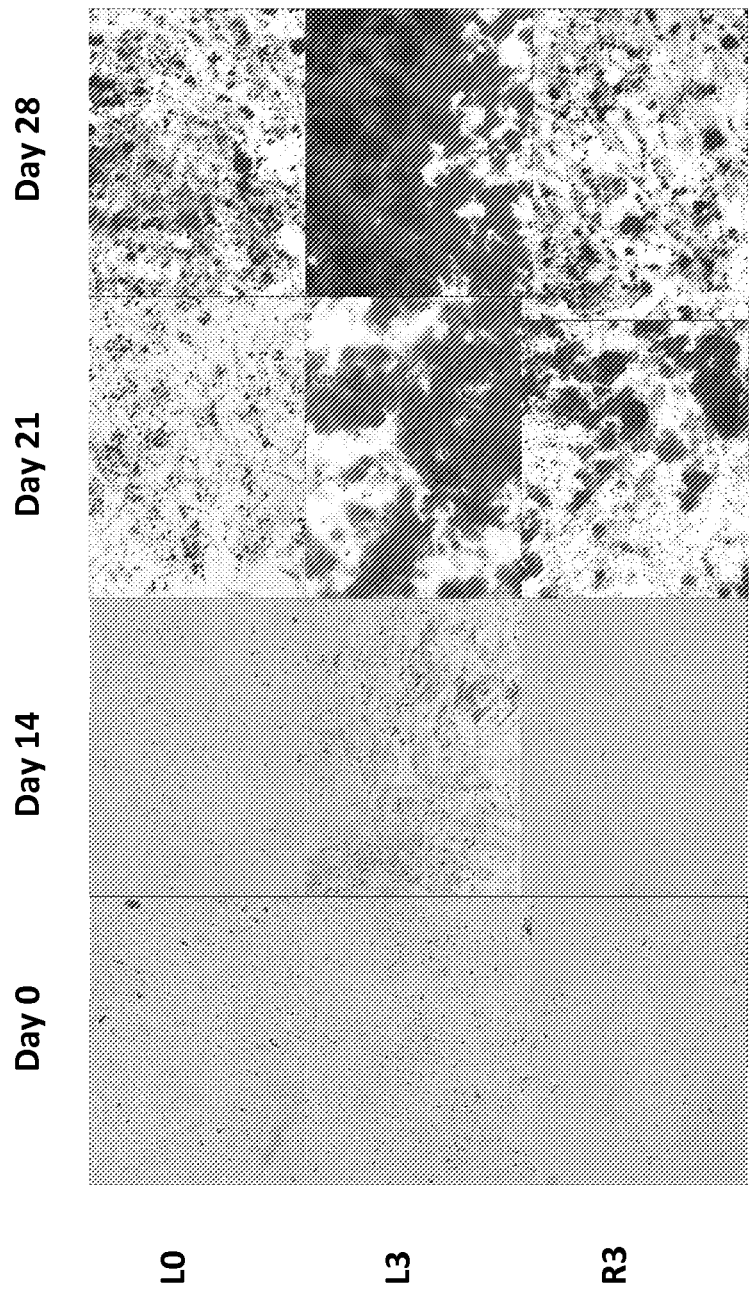

FIG. 12 represents the in situ calcium labeling of cells treated as in FIG. 10, but grown for up to 28 days.

FIG. 13 represents bone reconstruction of a patient's jaw using stem cells obtained according to the invention (in larger amount). Left: one week after treatment, showing the implant filled with 12 cm$^3$ heterologous bone; Right: after 54 Days of treatment, disclosing the homogenous tissue reformed and neo-formatted bone tissue recovering the implant. Lower panel: $^{99}$Tc scintigraphy 90 Days after the treatment evidencing that reconstructed jaw is made of living tissue (angiogenesis).

DETAILED DESCRIPTION OF THE INVENTION

In the present method, a human patient is used both as the donor and as the host for the graft.

The originality of the present method is that the proliferation cell step is performed in situ i.e. in vivo and no longer in vitro as done in the prior art techniques. However, stem cells stimulated according to the invention, have an increased growth in vitro (compared to non stimulated stem cells). It is known that the amount of stem cells produced by a human patient is extremely important in newborn humans, but decreases rapidly with years.

Therefore, it is extremely difficult to recover stem cells from patients, especially older patients.

Therefore, the method and means according to the invention can be used for obtaining rapidly in vivo large amount of stem cells and recover these obtained stem cells with limited risk to the patient.

This technical characteristic combined with the use of activated autologous PRP confers to the present method and means a real advantage over the prior art in terms of efficiency.

Indeed, the risk of graft rejection is thus minimized, and the safety of the method is optimized, as in vitro manipulation is (or can be) minimized.

In addition, the inventors observed that, advantageously, the white cell content is almost unchanged in the patient's blood upon the method the developed and/or after the use of PRP and a coagulation factor according to the invention.

However, several steps especially cellular differentiation could be realized in vitro.

It will be also demonstrated that culture media enriched with PRP and soluble hTf are more potent in inducing stem cell proliferation in vitro, and also in keeping them undifferentiated.

A blood (fluid) sample from about 20 to about 200 ml, preferably about 60 ml of blood from a human patient is collected. From this collected blood sample, it is possible to obtain a preparation of an autologous platelet rich plasma (autologous PRP) (about 6 or about 7 to about 40 ml of PRP, preferably about 7 to about 10 ml of PRP) which comprises a concentration of platelets (between about 100% and about 1000% or higher of the original concentration in total blood of the human patient) by Magellan™ Medtronic® method and apparatus or devices described in the state of the art (WO03106040, WO00/61256, WO2004/024198, U.S. Pat. No. 6,855,119, WO02/080991 and U.S. Pat. No. 6,719,901).

The obtained autologous platelet-rich plasma is added to a coagulation factor (about 200 to about 10000 units of thrombin or about 1 mg recombinant human tissue factor (thromboplastin)) in dry form per microliter, to form a first solution containing concentrated activated autologous PRP.

The platelet concentration is adapted to ensure viability of the platelets at about 37° C.

Alternatively, instead of adding thrombin or recombinant soluble human tissue factor (thromboplastin) to said autologous platelet-rich plasma, the autologous PRP can be re-injected in the iliac crest, the sternum or fat (adipose) tissue of the same human patient, preferably using the present permanent implantable means suitable for delivering and/or withdrawing fluids to and/or from the bone marrow cavity.

The coagulation factors (or $CaCl_2$) are added to the syringe of PRP just before injection.

This solution is re-injected in the iliac crest, the sternum and/or a fat (adipose) tissue of the same human patient, so as to locally induce in said patient an in vivo proliferation of (mesenchymal and/or endothelial progenitors, but without advantageously induce a proliferation of HSC) stem cells.

About 3, 4, 5, 6, 7, 8, 9, 10, 11, 12, 13, 14, 15, 16, 17, 18, 19, 20 to about 21 days after the injection, a bone marrow sample rich in (mesenchymal) stem cells was collected (at the same target injection site). After 3 days and 7 days, 10 ml of blood and bone marrow samples were collected to estimate the eventual modifications of hematological parameters (hematocrit, hemoglobin, leucocyte). After 3 days and 7 days, bone marrow samples were collected by two punctions which are made in opposite to each other to compare EPC, and MSC and to evidence the mobilization of stem cells in peripheral blood.

This collecting step is done the same day as proposed, for instance for the orthopedic or for the chirurgical treatment method.

These collecting steps are preferably repeated several times at defined time intervals (preferably every week) so as to obtain a sufficient stem cells concentration.

Platelets are known to release a number of molecules including platelet-derived growth factor, transforming growth factor beta, platelet-derived epidermal growth factor, platelet-derived angiogenesis factor, insulin-like growth factor 1 and platelet growth factor 4. These molecules signal the local mesenchymal and epithelial cells to migrate, divide, and increase collagen and matrix synthesis.

Furthermore, the bone marrow sample previously collected is mixed with platelet rich plasma (preferably in addition to an amount of about 1 mg of a recombinant human tissue factor (thromboplastin)) or of a sufficient amount of one of the above described coagulation factor so as to obtain a composition comprising the activated and concentrated autologous PRP and MSC.

Furthermore, an amount of about 80 mg/ml of vitamin C (L-Ascorbic acid), vitamin D3 (1,25(OH)2D3 vitamin) and a concentration of about $10^{-8}$ M of dexamethasone may be added to this concentration in order to induce proliferation, differentiation and matrix production. The dexamethasone is preferably prepared with PLGA (poly DL-lactic-co glycolic acid), PGA (vp8) (polyglycolic acid), PLLA (poly-L-lactic acid) and/or alginate scaffolds (such as microbeads) which allow (delayed) release of an encapsulated compound. Other polymeric compounds could be used for obtaining an efficient encapsulation and release of these preferred compounds.

Such scaffold comprising an active compound for enhancing bone formation is similar to the one already described in the scientific literature (Mariani M. et al, Tissue Eng. 12(3), pp. 547-558 (2006) and Inane B. et al., Tissue Eng. 12 (2) pp. 257-266 (2006).

The obtained composition is similar to a gel which also comprises an adequate gelling agent (such as alginate or $CaCl_2$ solution), so as to form a paste which could be directly used for bone tissue regeneration (see WO2004/024198). This could be adapted by the person skilled in the art for obtaining an efficient expansion and/or differentiation.

Furthermore, some phenotype markers, expressed by cells (CD34, CD133, CD45, NGF-R, cytokines produced, . . . ) at different steps can be used to follow the expansion and/or differentiation of stem cells into immature cells (immature osteoprogenitor cells), mature osteoprogenitor cells, preosteoblastic cells, mature osteoblast cells, osteocyte cells, etc.

Other compounds, such as transcriptional regulators (Cbfa-1, Msx-2 c-fos, fra-2, Dix-5, . . . ) lymphokines (IL-1), growth factor (TGF-β), (EGF) can also be used in the methods and compositions of the invention.

Figure 1:
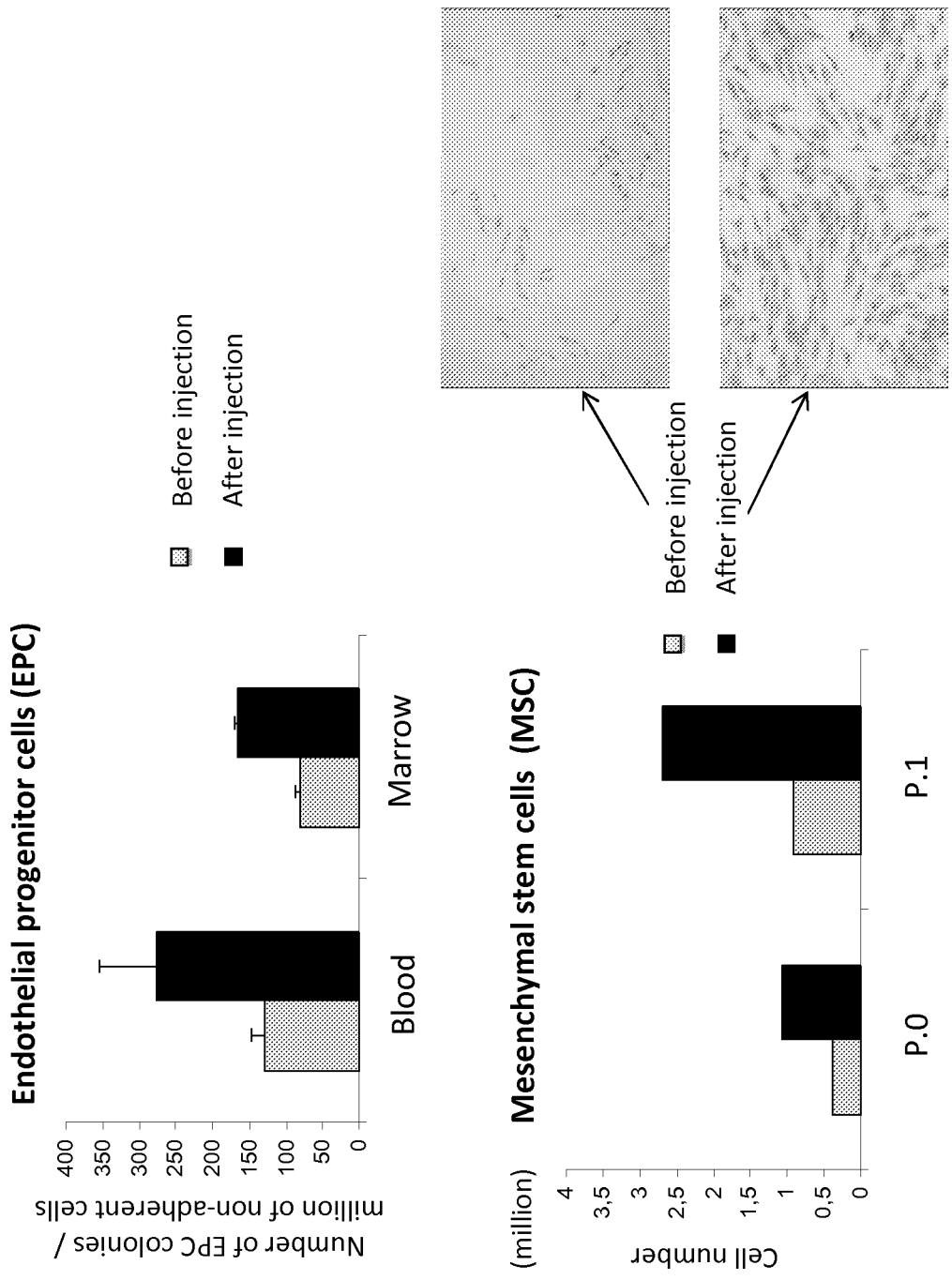
Figure 4:
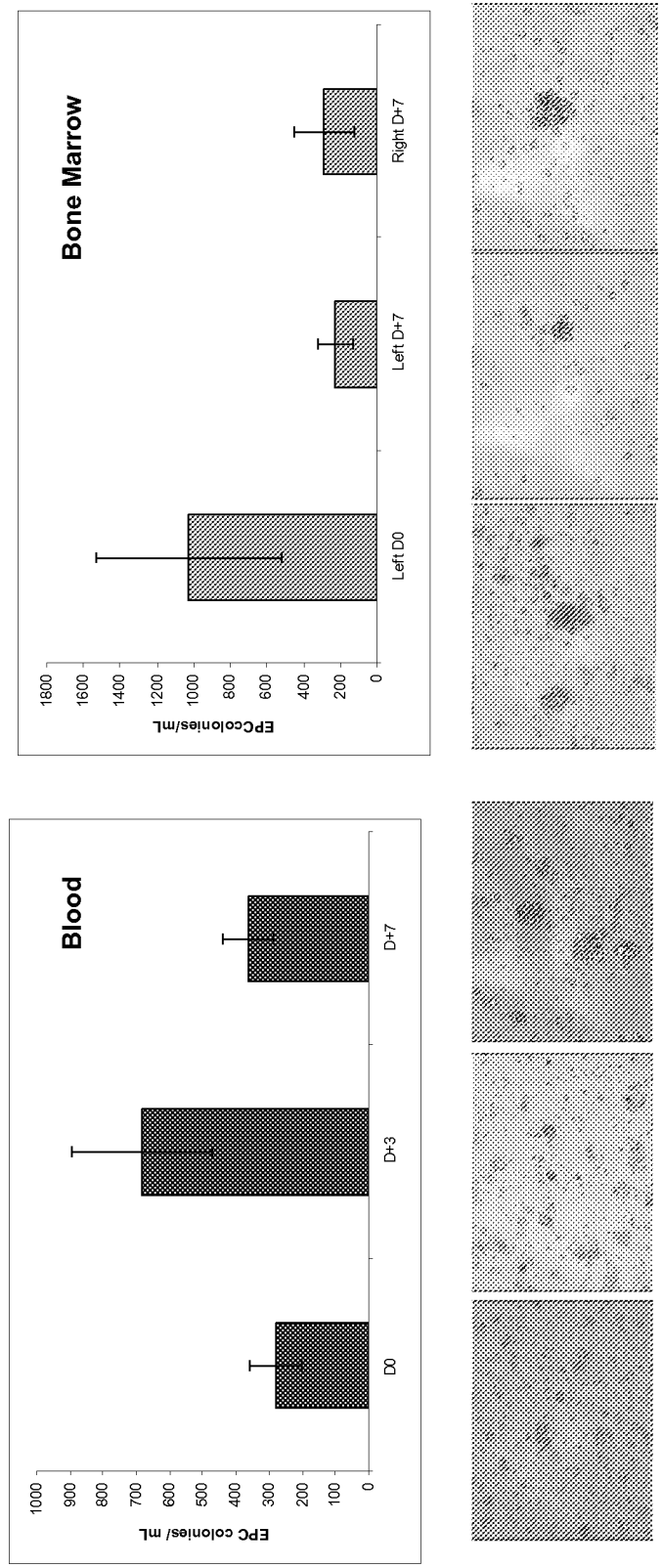

A first type of stem cells being $CD34^+$ and $CD31^+$ in the bone marrow was obtained. The FIGS. 1 and 2 show that, with the method of the invention, it is possible to obtain a stimulation in vivo (by addition of PRP and tissue factor: 20 to 1000 μg soluble tissue factor (sTF)/6 ml PRP, preferably 100-700 μg sTF/6 ml PRP, more preferably 334 μg sTF/6 ml of PRP) of EPC in the bone marrow and in the peripheral blood. Furthermore, MSC are also significantly and unexpectedly amplified before and after the primo culture (FIG. 7).

TABLE 1

Changes of cell population, including stem cells, after sTF-PRP injection of the human posterior iliac crest (left side) in the bone marrow (BM).

| | Left BM Day 0 | Left BM Day 7 | Right BM Day 7 |
|---|---|---|---|
| WBC ($10^9$/L) | 11.85 ± 3.0 | 22.67 ± 2.2 (×1.9) | 11.0 ± 1.87 (×0.9) |
| $CD34^+$ • | 0.5 ± 0.14 | 0.81 ± 0.36 (×1.6) | 0.72 ± 0.13 (×1.4) |
| $CD133^+$ • | 0.3 ± 0.07 | 0.47 ± 0.76 (×1.55) | 0.58 ± 0.43 (×1.9) |
| CFU-F * | 30 ± 9 | 125 ± 50 (×4.1) | 10 ± 8 (×0.3) |
| CFU-C □ | 43 ± 11 | 56.5 ± 16 (×1.3) | 17 ± 7 (×0.4) |

WBC white blood count
• % positive cells
* colony forming unit-fibroblasts for $10^6$ mononuclear cells
□ hematopoietic colony forming unit (comprising CFU-GM, BFU-e and CFU-e for 4 × $10^4$ mononuclear cells)
Values represent mean ± SEM (n = 5 healthy persons from 40 to 55 year old).

From Table 1, at day 7 post-treatment, 'daughter-cells' content such as WBC, and CFU-F is strongly enhanced at the injection-side of the bone-marrow. In practice, this effect is even bigger. Indeed, this quantification does not count the mobilization of cells to the blood, as exemplified by the reduction of the CFU-F and -C contents in the side opposite the injection and evidenced in FIG. 3. and FIG. 7. This first evidence of mobilization, even in the case of healthy patients, shows the potential for therapeutic purpose. Moreover, other 'daughter cells', i.e. EPC as demonstrated in FIG. 1, are mobilized in the blood and remain surprisingly (more) abundant in the bone marrow (see FIG. 2), reflecting a complex kinetics of stimulation (multiplication) followed by differentiation and mobilization.

The inventor then measured the capacity of the treated cells to form colonies. As shown in FIG. 3, cells are obtained from the blood and from the bone marrow. As shown above, 3 days after PRP+soluble hTf injection, the number of EPC colonies is increased by more than two fold. This effect is sustained through Day 7. In the bone marrow however, the number of EPC colonies decreased at day 7, reflecting their mobilization.

Figure 5:
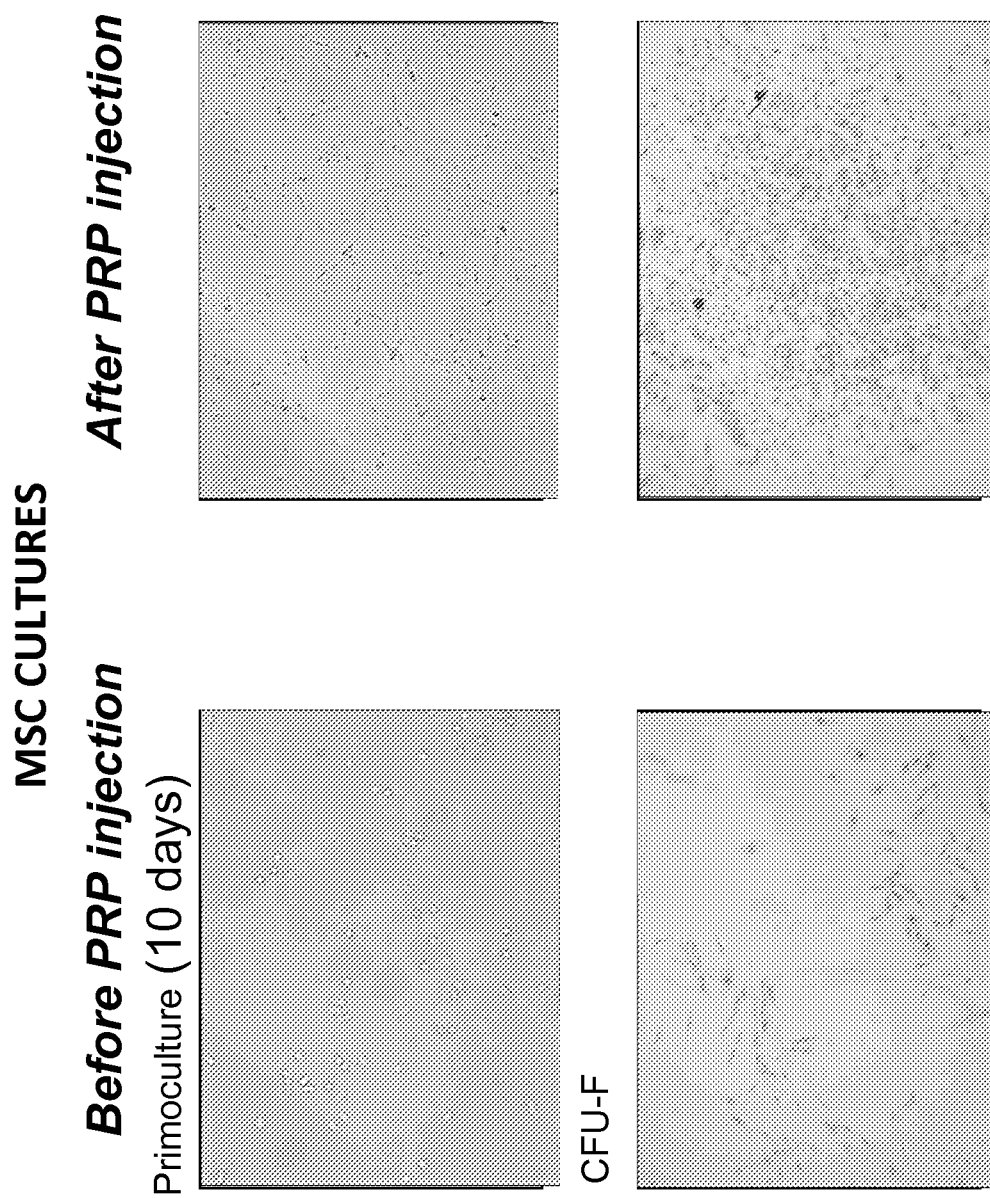
FIG. 5 represents the in vitro culture of MSC after PRP injection.

The MSC were taken from the bone marrow after 7 days of PRP+soluble hTf injection and then grown on Petri dishes (FIG. 5). Much more CFU-F were obtained from the bone marrow after PRP+soluble hTf injection.

Figure 6:
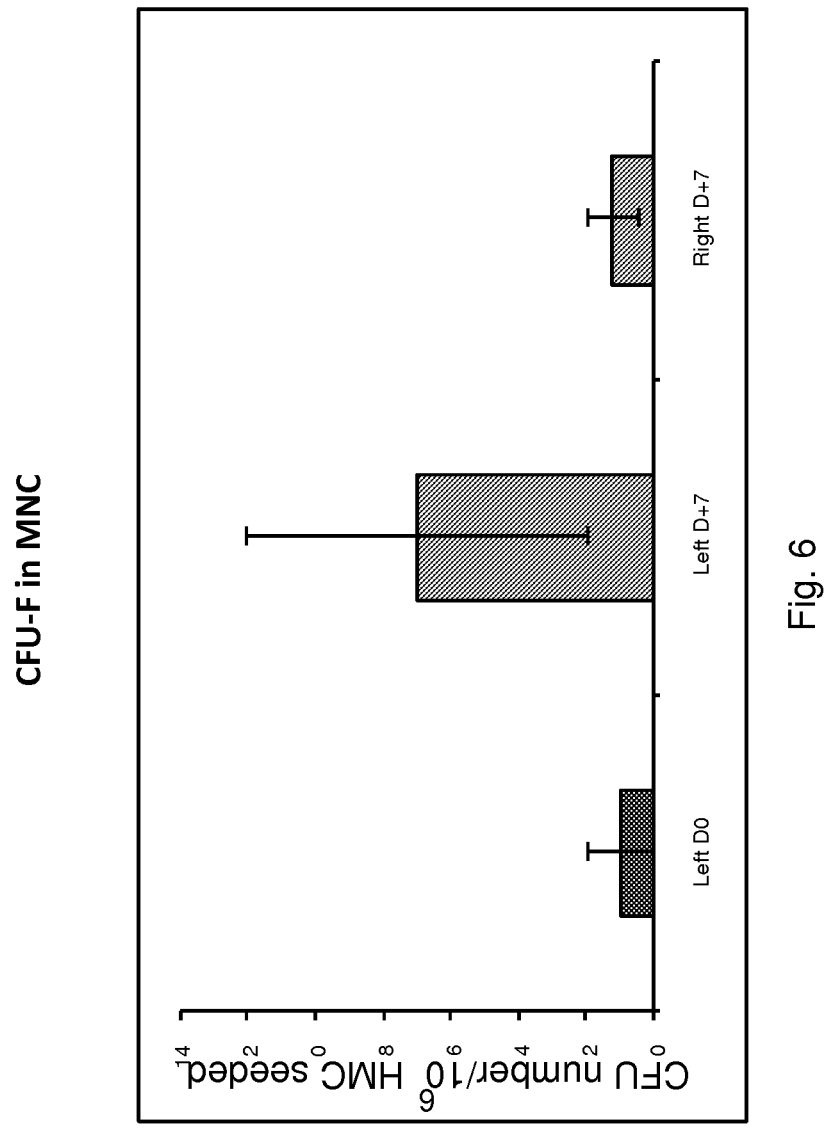
FIG. 6 represents the increase of Colony-Forming Unit Fibroblasts (CFU-F) in the stimulation zone.

The inventor purified mononuclear cells (MNC) taken from the bone marrow before or after 7 days of treatment and measured a tree-fold increase of their capacity to form colonies (FIG. 6).

The MSC were taken from the bone marrow before or after 7 days of PRP+soluble hTf injection and then grown (FIG. 7). The cells taken from the treated site, besides being more abundant, had acquired an increased capacity to grow in vitro.

The inventor then characterized cells in the blood (FIG. 8) and in the bone marrow (FIG. 9). In the blood, CD 34 and CD 133 cells were increased by the treatment, disclosing a positive effect of the treatment on stem cells growth and mobilization, while their relative abundance remained constant in the bone marrow, reflecting the capacity of the bone marrow to keep the stem content constant. The inventor further noticed that, following the treatment, CD31 cells were more abundant in the bone marrow This kinetics is related to the cell-type and the hierarchy: more rapid for 'mothers' $CD34^+$ and $CD133^+$, whose levels almost returned to the baseline at day 7 and slower for 'daughters' EPC and CFU-F stem cells, whose level are higher at day 7 on the side of injection, and probably even slower for differentiated WBC.

A mineral type matrix obtained from a xenograft, an allograft or an autograft can also be used in a gel composition for improving bone regeneration tissue.

For obtaining differentiation of the stem cells into specific tissues, it is possible to use some specific growth factors for obtaining regeneration of specific tissue (epidermal growth factor EGF) for obtaining skin tissue, BMP family compound to induce formation of bone or cartilage, G-CSF or AMD300 for inducing hematopoetic differentiation etc.

The gel composition could also comprise other elements in order to expand and differentiate stem cells into the required tissue cells, through a complex cascade of events involving sequential proliferation, differentiation, maturation and possibly mineralization (for obtaining osteoblastic cells). This gel composition may also comprise β glycerol-phosphate (for inducing dystrophic mineral deposit formation), some more specific human growth factors, or calcium containing compounds (such as $CaCl_2$, β-tricalciumphosphate, bone particles (from denatured bone or not), apatite, aspidine, calcium sulfate, calcium carbonate, hydroxyapatite, calcium gluconolactate, calcium gluconate, calcium lactate, calcium glutoniate and mixture thereof) examples of such compounds are described in EP 1239894.

The inventor stimulated stem cells as above described, then measured their increased capacity to form colonies, to express alkaline phosphatase, to use and fix calcium (FIGS. 10 to 12).

Thereafter, the inventor used the obtained cells to produce an autologous implant and reconstitute the complete bone.

As shown in FIG. 13, the inventor was able to reconstitute living tissue after having activated stem cells by the injection of PRP and soluble hTf into the bone marrow, then obtained stem cells 3 days after the activation. After 3 days of activation, there was a 7-fold increase of endothelial progenitor cells in the blood, while there was a two-fold increase in the bone marrow, reflecting both the multiplication and the mobilization of stem cells three days after the treatment. These stem cells were deposited on a titanium mesh adapted to be placed in a patient's damaged jaw. These activated stem cells were able to grow, to differentiate and to reconstitute living tissue, including producing new blood vessels, as depicted by $^{99}Tc$ scintigraphy.

The inventor then searched for any change in the blood concentration of cytokines in 13 patients treated according to the present invention. There was a considerable increase in FGF-2 (about 4-fold), of VEGF (about 2-fold), of Rantes (about 2-fold) and of BDNF (+50 percent), 3 days and 7 days after the injection of PRP and a coagulation factor (shTf) in the bone marrow of the iliac crest of the said patients.

The inventor then tested the injection of PRP and a coagulation factor (shTf) in patients suffering from neuro-degenerative (neurological) disease, having the intention to slow them or even to stop them. The inventor selected patients suffering from amyotrophic lateral sclerosis (ALS) and injected the PRP and a coagulation factor (shTf) in the bone marrow from the iliac crest at the left side then, four days later, he performed again the same injection at the right side and repeated this protocol for one month and allowed the patient to recover for one month without such injections. Then this injection protocol was repeated and a reduction in worsening of the disease and even some improvements was obtained.

Then he further evaluated his invention in cardiology (patients having suffered from a myocardial infarction) by recovering stem cells of the bone marrow of patients three days after injection of PRP and a coagulation factor (shTf), then purified the (MSC-enriched) stem cells from the activated bone marrow by centrifugation at 2 000 g×min for 5 minutes before re-injecting enriched stem cells (MSC) into the heart of the patients. Overall the inventor noticed improvement in patients treated following the teachings of the present invention.

The inventor further stimulated the proliferation and activation of stem cells by injecting the PRP and a coagulation factor (shTf) in the bone marrow from the iliac crest of a compatible donor. Then the inventor isolated a (activated) bone-marrow sample from this donor, before reinjection to a patient suffering of leukemia whose bone marrow has been irradiated.

The inventor then evaluated his invention in infectious diseases (AIDS).

It is however clear that, given the increase of stem cells and/or of cytokines caused by the method and/or the pharmaceutical product of the invention, several other diseases can be treated by the skilled person, the said diseases being preferably selected from the group consisting of cardiologic, neurologic, degenerative diseases including cancer, inflammation, osteoporosis, hepatic injury, auto-immune diseases and/or infectious diseases.

The invention claimed is:

1. A method for obtaining non-embryonic mammalian stem cells comprising the steps of:
   a) collecting a first blood sample from a mammalian subject;
   b) preparing an autologous platelet-rich plasma (PRP) from the first blood sample;
   c) activating said autologous PRP by addition of an effective amount of soluble human thromboplastin to obtain a first fluid containing concentrated activated autologous PRP;
   d) selecting in the mammalian subject a target injection area comprising non-embryonic stem cells, wherein the target injection area is selected from bone marrow or fat tissue;
   e) injecting the first fluid into the target injection area of the mammalian subject to locally induce in said mammalian subject in vivo proliferation of the non-embryonic stem cells; and
   f) after an incubation time, collecting from the mammalian subject injected with the first fluid a second blood sample and/or a bone marrow sample comprising stem cells and recovering the stem cells from the second blood sample and/or the bone marrow sample, wherein the non-embryonic stem cells include mesenchymal stem cells and endothelial progenitor cells.

2. The method according to claim 1 comprising the steps of repeating step a) to step e) or step a) to step f) several times.

3. The method according to claim 1, further comprising:
   g) collecting a third blood sample from the mammalian subject injected with the first fluid,
   h) preparing a second autologous PRP from the third blood sample;
   i) activating said second autologous PRP by addition of an effective amount of soluble human thromboplastin so as to obtain a second fluid containing concentrated activated autologous PRP;
   j) mixing the second fluid and the recovered stem cells from step f) to obtain a composition comprising activated concentrated autologous PRP and stem cells;
   k) adding differentiation adjuvants to the composition of step j), wherein the adjuvants comprise at least one matrix for cell anchoring and another element selected from the group consisting of vitamins, cortisone, dexamethasone, hydrocortisone, prednisolone, methylprednisolone, triamcinolone, betamethasone and β-glycerophosphate, to induce a differentiation of the stem cells into differentiated bone tissue cells.

4. The method according to the claim 3, further comprising the step of:
   l) adding to the composition comprising activated concentrated autologous PRP and stem cells, a gelling agent to form a gel composition, and
   m) applying the gel composition to a target tissue reconstruction site of the mammalian subject, so that tissue reconstruction can take place at the reconstruction site.

5. The method according to the claim 1, wherein the incubation time is between about 3 days and about 3 months.

6. The method according to the claim 1, wherein the autologous PRP comprises between about 600,000 platelets per microliter and about 8,000,000 platelets per microliter.

7. A method for obtaining a cell population enriched in activated mesenchymal stem cells (MSC), comprising the steps of activating bone marrow by injecting PRP and soluble human thromboplastin in vivo; obtaining a sample from the activated bone marrow; and enriching stem cells including MSC present in the bone marrow sample.

8. The method according to claim 7, wherein the enriching of stem cells is performed by centrifugation of the bone marrow sample and by recovering of an intermediate fraction of stem cells.

9. The method according to claim 7, wherein the method increases a capacity of the MSC to form colonies.

10. The method according to the claim 9, wherein capacity of the MSC to form colonies is increased by at least about 30% and/or wherein at least 13 MSC colonies are obtained when culturing 1,000,000 mononuclear cells of a sample obtained from the activated bone marrow.

11. The method of claim 1, wherein the target injection area is sternum or iliac crest bone marrow.

* * * * *